United States Patent [19]

Nies et al.

[11] Patent Number: 5,650,108
[45] Date of Patent: Jul. 22, 1997

[54] POROUS BONE REPLACEMENT MATERIALS

[75] Inventors: Berthold Nies, Frankisch-Crumbach; Sabine Troster, Langen; Rainer Specht, Furth, all of Germany

[73] Assignee: Merck Patent Gesellschaft mit beschrankter Haftung, Darmstadt, Germany

[21] Appl. No.: 538,829

[22] Filed: Oct. 5, 1995

[30] Foreign Application Priority Data

Oct. 6, 1994 [DE] Germany ............... 44 35 680.3

[51] Int. Cl.$^6$ ............... A61F 2/28; A61F 2/02
[52] U.S. Cl. ............... 264/122; 264/109; 623/16
[58] Field of Search ............... 264/109, 122; 623/16

[56] References Cited

U.S. PATENT DOCUMENTS

| | | | |
|---|---|---|---|
| 5,356,629 | 10/1994 | Sander et al. | 623/165 |
| 5,370,692 | 12/1994 | Fink et al. | 623/16 |
| 5,425,770 | 6/1995 | Piez et al. | 623/16 |
| 5,538,514 | 7/1996 | Hawkins | 623/16 |

FOREIGN PATENT DOCUMENTS

| | | |
|---|---|---|
| 16906 | 10/1980 | European Pat. Off. |
| 519293 | 12/1992 | European Pat. Off. |
| 85/00291 | 1/1985 | WIPO |

*Primary Examiner*—Mary Lynn Theisen
*Attorney, Agent, or Firm*—Millen, White, Zelano, & Branigan, P.C.

[57] ABSTRACT

A process for the preparation of porous bone replacement materials which have a partly or completely interconnecting pore system with a volume content of 5 to 60%. The bone replacement material is prepared from a mixture of a solid component, a liquid component based on acrylate/methacrylate and coarse-particled granules of a biocompatible material with an average particle diameter of 0.5 to 10 mm.

15 Claims, No Drawings

POROUS BONE REPLACEMENT MATERIALS

The invention relates to porous bone replacement materials, and in particular to a process for their preparation.

BACKGROUND OF THE INVENTION

Bone cements based on acrylate plastics and bone replacement materials prepared therefrom have been known for a long time. Polymer materials based on acrylic and/or methacrylic acid esters have proved suitable therefor because of their biocompatibility, their outstanding strength properties, their favorable properties regarding release of embedded pharmaceutical active compounds and, last but not least, because of their processability appropriate for their use.

The usual bone cements are composed of a solid component, which comprises a finely divided polymer of acrylic and/or methacrylic acid esters and further additives, such as polymerization catalysts and, if appropriate, X-ray contrast media, fillers and dyestuffs, and a liquid component, which comprises an acrylic and/or methacrylic acid ester monomer and further additives, such as polymerization accelerators and stabilizers. For use, the solid component and liquid component are mixed to give a liquid to semi-solid paste, and this is brought into a desired shape, if appropriate, or applied to the implantation site for cementing in a prosthesis. The composition is hardened completely by the polymerization reaction induced when the components are mixed. The bone cement is expediently provided in a form in which separate containers with amounts of the two components which are coordinated with one another are combined as a pack unit. As a general rule, the proportion of solid component is about 50 to 75% by weight and the proportion of liquid component is about 50 to 25% by weight.

A bone cement which, in a normal pack, comprises two sachets of about 40 g of polymer powder each and 2 ampoules of 20 ml of monomer liquid each, for example, is very common. The powder is a fine bead polymer of methyl methacrylate with a copolymer content of methyl acrylate. About 0.5% of dibenzoyl peroxide is added to the powder as a catalyst. Small amounts of chlorophyll are also copolymerized during preparation for identification of the material. The powder additionally comprises a customary X-ray contrast medium, such as, for example, zirconium dioxide. The associated liquid comprises monomeric methyl methacrylate, to which about 0.7% of dimethyl-p-toluidine is added as a polymerization accelerator and small amounts of hydroquinone are added as a stabilizer. This liquid is also usually colored with a small amount of chlorophyll for identification. The powder, which is packed in polyethylene sachets, is sterilized with ethylene oxide. The liquid is subjected to sterile filtration and dispensed into glass ampoules.

When 2 parts by weight of powder are mixed together with one part by weight of liquid, dibenzoyl peroxide reacts with the dimethyl-p-toluidine in the liquid, and free radical polymerization is initiated by this means. The mixture is coordinated such that it can be used as a doughy paste after only about one minute. This paste remains kneadable for several minutes and then starts to harden, with evolution of heat. After about 5 to 10 minutes, the polymerization has essentially ended. During the polymerization phase, as long as the paste can still be shaped, it can be brought into any desired shape, that is to say, for example, can be introduced directly into the body for filling bone cavities or for cementing in prostheses, or can be used for the production of shaped articles which harden extra-corporeally and can then be used at any desired positions in the body.

While the clinical results with such bone cements are chiefly very good with implantation of endoprostheses, the prosthesis as a general rule being surrounded only by a uniform thin cement sheath which provides the bond between the prosthesis and the bone bed, problems as far as clinical failure often arise if relatively large amounts of cement in thick layers are necessary because of the implantation conditions or the field of use. This is the case, for example, if relatively large bone defects which must be filled with bone cement are present when a prosthesis is changed or after resection of bone tumors. One reason for the problems which occur lies in the exothermic polymerization reaction during hardening of the bone cement. Significant increases in temperature occur in cement thicknesses above about 4 mm, since the heat of reaction developed can no longer be distributed and removed adequately. For example, a temperature of about 100° C. can easily be reached inside a cylindrical shaped article of bone cement of about 3 cm diameter during hardening. Heat necroses in the bone bed or in tissue surrounding the implantation site are the consequence.

Another problem factor is the shrinkage of bone cement based on acrylate, which is of more consequence the thicker the cement layer. This causes damage to the implant bed, which can lead to premature loosening right up to breakage of the prosthesis.

The strongest possible bond with the original bone or its fragments is the aim in the case of implantation of endoprostheses and also in the case of implantable shaped articles for bone replacement in the context of osteosynthesis. This can be achieved effectively only with intimate meshing, extending ideally to complete growth of regenerated bone matrix throughout the implant material. Nevertheless, a precondition of this is an adequate porosity, ideally with an interconnecting pore system, of the bone replacement material.

Bone replacement materials having a porous and, where appropriate, also interconnecting pore structure with a high mechanical stability at the same time are known. However, these are essentially ceramic shaped articles which are obtained by sintering, for example, calcium phosphate materials, such as hydroxyapatite or tricalcium phosphate, or by pyrolysis and sintering of natural bone. With these materials, it is of course possible only to fill bone defects.

A porous implant material with an interconnecting pore system based on calcium phosphate ceramic particles and bioabsorbable polymer is known from EP 0 519 293 A1. This material is also suitable only for filling bone defects, and because of its low mechanical strength is unsuitable for replacement of high-load bone structures. Although this material is plastically deformable to a certain extent, it is not suitable for anchoring endoprostheses in the sense of bone cement.

The lowest possible porosity is aimed for in customary bone cements for reasons of the mechanical strength required of the prosthesis-bone cement-bone bed bond. For this reason, the bone cement components are preferably mixed in vacuo with subsequent compression, so that inclusions of air and the resulting pore formation are avoided here as far as possible. To improve the long-term bond with the bone bed, it is advantageous to add osteoconductive additives to the bone cement. Possible such additives are chiefly finely divided calcium phosphate materials, such as hydroxyapatite and tricalcium phosphate, which are more or less bioabsorbable. Such bone cements which can comprise up to 35% by weight of such calcium phosphates having a particle size of up to 300 μm are known from EP 0 016 906 and EP 0 148 253. However, these particles are for the most part embedded in the polymer material of the bone cement and enclosed by this. A certain porosity into which the bone matrix can grow can therefore only develop in the course of healing of the cemented prosthesis or of the bone cement implant into the surface regions of the bone cement in contact with the bone bed by absorption of calcium phosphate particles on the surface.

SUMMARY OF THE INVENTION

An object of this invention is the discovery of a bone replacement material which is equally suitable as a bone cement for anchoring endoprostheses and for production of shaped implant articles and which has a porosity with a pore system which interconnects as far as possible, coupled with an adequate mechanical strength.

Upon further study of the specification and appended claims, further objects and advantages of this invention will become apparent to those skilled in the art.

It has now been found that such a bone replacement material can be obtained if (a) preferably about 0 to 48% by weight of a solid component comprising a finely divided polymer of acrylic and/or methacrylic acid esters and, if appropriate, further additives, such as polymerization catalysts, X-ray contrast media, fillers and dyes, (b) preferably about 2 to 50% by weight of a liquid component comprising an acrylic and/or methacrylic acid ester monomer and, if appropriate, further additives, such as polymerization accelerators and stabilizers, and (c) preferably about 50 to 98% by weight of coarse-particled granules of a biocompatible material having an average particle diameter of preferably about 0.5 to 10 mm are mixed with one another, and the mixture is brought into a desired shape, if appropriate, and then hardened. A bone replacement material with a partly or completely interconnecting pore system with a volume content of 5 to 60% is obtained by this procedure.

The invention thus relates to a process as characterized above for the preparation of porous bone replacement materials which have a partly or completely interconnecting pore system with a volume content of 5 to 60%.

All the customary bone cements based on acrylate/methacrylate and the starting substances usual for these materials can be used in the process according to the invention. Bone cements of this type are commercially obtainable. The expert is familiar with their composition and the nature of their processing.

According to the invention, coarse-particled granules of a biocompatible material with an average particle diameter of preferably about 0.5 to 10 mm form a considerable proportion, that is to say preferably about 50 to 98% by weight, based on the total amount, of the porous bone replacement material. The average particle diameter of the granules is preferably from 1–5 mm, and in particular about 3 mm. "Particle diameter" in the case of non-spherical or irregularly shaped particles is to be understood as meaning the longest axis which can be laid through the particle. The shape and size distribution of the granule particles can in principle be chosen as desired. In addition to essentially irregularly shaped particles, granule particles of spherical shape, approximately spherical shape and, in particular, cylindrical shape are preferred. Preferably, the particle size lies within a narrow range or is to a large extent uniform. The choice of shape and size of the particles is made according to the porosity required in the bone replacement material and the nature of the pore structure. Thus, for example, spherical particles lead to overall denser materials with geometrically more uniform pore characteristics, while approximately cylindrical or completely irregular particles lead to porous materials with a more irregular pore structure. Furthermore, coarse particles lead to larger pore diameters, while fine particles in turn cause a narrower pore system.

Possible starting materials for the coarse-particled granules are in principle all biocompatible plastics and biocompatible inorganic solids. Those materials which are customary and proven in endoprosthetics are preferably employed. Materials which form an intimate, strong bond with the components of bone cements, in particular with the hardened monomer, are particularly expedient. Preferred materials are accordingly based on polyacrylates and/or polymethacrylates. Polymers of this type are available in granule form in the desired size range of the granule particles, or can easily be processed to corresponding granules, for example by extrusion and comminution. It is particularly favorable if the bone cement base material itself is employed as the granule material. Such granules accordingly preferably comprise a hardened mixture of about 5 to 90% by weight of a solid component comprising a finely divided polymer of acrylic and/or methacrylic acid esters and, if appropriate, further additives, such as polymerization catalysts, X-ray contrast media, fillers and dyes, and about 95 to 10% by weight of a liquid component comprising an acrylic and/or methacrylic acid ester monomer and, if appropriate, further additives, such as polymerization accelerators and stabilizers. After hardening has taken place, such a bone cement mixture can be comminuted mechanically to the desired particle size. As a general rule, granule particles with irregular shaping result from this procedure. The freshly mixed bone cement can also be shaped to granule particles during the liquid or plastic phase, for example by extrusion. As a general rule, this results in cylindrical granule particles. An elegant method for the preparation of spherical bone cement particles is, for example, that of adding a freshly mixed low-viscosity bone cement dropwise to a stirred aqueous sodium alginate solution temperature-controlled at the reaction temperature. Polymer beads of about 0.5 to 3 mm diameter, depending on the nozzle size, the viscosity of the bone cement and the stirring speed of the alginate solution, can be produced by this procedure.

In addition to materials based on acrylate/methacrylate, it is also possible to use other plastics materials, such as polyolefins, copolymers of acrylates with styrene and/or butadiene and epoxy resins, for the preparation of granules.

Of the inorganic materials, calcium compounds, such as, in particular, calcium phosphate, are preferred. These are particularly preferably in the form of sintered calcium phosphate ceramics. Starting substances for the preparation of granules by methods known per se can be hydroxyapatite, tricalcium phosphate or pyrolyzed bone sintered to the ceramic material.

The solid component of the bone cement, which is usually present as a bead polymer of methyl methacrylate/methyl acrylate copolymer with average particle sizes of from about 5 to 250 μm, comprises a polymerization catalyst, such as, for example, dibenzoyl peroxide. It can furthermore comprise X-ray contrast media, such as, for example, zirconium dioxide, dyes for identification, such as, for example, chlorophyll, and fillers, and if appropriate further additives. The liquid monomer component methyl methacrylate as a general rule comprises a polymerization accelerator, such as dimethyl-p-toluidine, and hydroquinone, as a stabilizer, in the amounts customary for these compounds. As the liquid component also solutions or suspensions of oligomers and/or polymers of acrylates and/or methacrylates in the mentioned monomers may be used.

Dyes and other expedient additives can furthermore be present. Possible additives to the solid component and also to the coarse-particled granules are, in particular, osteoinductive and/or osteoconductive fillers, such as, for example, hydroxyapatite and tricalcium phosphate. The proportion of such additives can vary within a wide range and depends on the particular profile of requirements of the bone cement or of the corresponding secondary products. As a general rule, they should not exceed about 30% by weight, based on the solid component and on the coarse-particled granules.

All pharmaceutically active compounds which on the one hand are appropriate in bone cements, in bone replacement materials and in implantable drug depots from the point of view of their action profile and which on the other hand are sufficiently stable towards the constituents of bone cements and at the temperatures which result during hardening can furthermore be added to the bone cement according to the invention or its components. Possible active compounds are, preferably, cytostatics, such as methotrexate, cisplatin, cyclophosphamide, fluorouracil, doxorubicin and the like, antibiotics, such as gentamicin, clindamycin, vancomycin, teicoplanin and the like, and furthermore antiseptics as well as bone growth-promoting substances. As a general rule, a proportion of pharmaceutical active compound of 0.1 to 5% by weight, based on the total amount of bone cement, is sufficient; in individual cases, in particular for the preparation of implantable drug depots, the proportion of active compound can also be higher.

For its preparation, the porous bone replacement material is expediently provided in the form of a set composed of separate packs of the three main components. Component (a) comprises the solid component comprising a finely divided polymer of acrylic and/or methacrylic acid esters and, if appropriate, further additives, such as polymerization catalysts, X-ray contrast media, fillers and dyestuffs, the proportion of which is preferably about 0 to 48% by weight of the bone cement. Component (b), the liquid component, comprises an acrylic and/or methacrylic acid ester monomer and, if appropriate, further additives, such as polymerization accelerators and stabilizers, the proportion of which is preferably about 2 to 50% by weight of the bone replacement material. Component (c) comprises the coarse-particled granules of biocompatible material with an average particle diameter preferably of about 0.5 to 10 mm, the proportion of which is preferably about 50 to 98% by weight, based on the bone replacement material.

The amounts of the components are preferably coordinated with one another such that the total three pack contents are combined with one another. The amounts are coordinated according to the proposed intended use and according to whether a low-viscosity, a medium-viscosity or a high-viscosity mixture is desired. If necessary, the solid component and the granules have been subjected to final sterilization by means of radiation or ethylene oxide and the liquid monomer component has been subjected to sterile filtration and each component is dispensed under sterile conditions into a suitable packaging. If appropriate, the solid component (a) and the coarse-particled granules (c) can also be present as a mixture in one pack unit.

It is expedient to complement such set of components with a device for mixing and/or application of the bone cement. Appropriate devices are known and customary. Preferably, appropriate devices allow mixing of the bone cement in vacuo and combined application of the cement by means of a bone cement syringe.

The ready-to-use porous bone cement or bone replacement material is prepared and further processed completely analogously to bone cement systems to date. The three main components are brought together and mixed with one another. After intimate thorough mixing of the components, the polymerization starts due to the catalyst contained therein; the mass remains liquid to plastically deformable generally for a period of a few minutes; thereafter, the hardened end product exists.

A finely porous to coarse-pored material is obtained thereby, depending on the amounts of the three main components and on the particle shape and particle size of the granules, it being possible for the volume content of the pores to range from 5 to 60%.

The development of a partly to completely interconnecting pore system is a preferred characteristic of the invention. Surprisingly, it is found that only a slight increase in temperature is to be detected during hardening of masses, even those of large volume. When applied in the living organism, heat necroses are therefore to be excluded. In the hardened state, the porous bone replacement material has an outstanding mechanical stability, such as, in particular, a high compressive strength.

During the liquid or plastic stage, the porous bone replacement material can be used in the customary manner as a bone cement for implantation of bone prostheses. The surgeon can also process the mass to shaped articles of any shape and size and, after hardening, can implant these into the regions of the body to be treated for restructuring of bone defects or as a local active compound depot. Such implantable shaped articles or drug depots can also be provided in ready-made form.

Without further elaboration, it is believed that one skilled in the art can, using the preceding description, utilize the present invention to its fullest extent. The preferred specific embodiments are, therefore, to be construed as merely illustrative, and not limitative of the disclosure in any way whatsoever.

The entire disclosure of all applications, patents and publications, cited above, and of corresponding German applications P 44 35 680.3, filed Oct. 6, 1994, are hereby incorporated by reference.

EXAMPLES

Example 1

Low-viscosity bone cement having a composition of 31 g of polymethyl methacrylate/polymethyl acrylate (94/6) copolymer, 6 g of hydroxyapatite powder and 3 g of zirconium dioxide is stirred with 30 ml of methyl methacrylate monomer in the customary manner. The components comprise the initiator system of dibenzoyl peroxide/dimethyl-p-toluidine. 100 g of pure, cylindrical polymethyl methacrylate granules (diameter 2 mm, length 3 mm) are added to this paste and mixed thoroughly with the bone cement paste. The mixed mass is introduced into polypropylene molds (diameter 30 mm, height 10 mm), and hardens after a period of about 15 minutes. A body with interconnecting pores and having a porosity of 20% results. Measurement of the temperature during the hardening shows a maximum value of 37° C. The compressive strength reaches a value of 60 MPa.

Example 2

As Example 1, but using a copolymer mixture, as the bone cement, having the composition of 80% of polymethyl methacrylate/polymethyl acrylate (94/6)+20% of polymethyl methacrylate/polymethyl acrylate (52/48). A bone cement of standard viscosity which, when mixed as mentioned, leads to an easily shapable bone replacement is obtained by this procedure. The polymerization time is about 9 minutes. This variant is suitable above all for application of the plastic mass into the bone and hardening in situ.

Example 3

A viscous suspension is prepared from a mixture of 95 g of polymethyl methacrylate bead polymer (diameter 30–80 pm), 5 g of polymethyl methacrylate/polymethyl acrylate (52/48) copolymer, 25 g of hydroxyapatite powder (2–5 µm) and 10 g of zirconium dioxide powder by addition of 70 ml of methyl methacrylate. A usual starter system is added. A 2% solution of Na alginate is stirred uniformly in a 2 l glass beaker and heated to 50° C. The suspension is added dropwise to the alginate solution, while continuing to stir, so that beads which are as uniform as possible result. Under the conditions mentioned, the beads polymerize in the course of about 5 minutes to give solid particles, which settle on the bottom after the stirrer has been switched off. The particles are separated off, washed, dried and classified.

The separated 1–2 mm fraction of such particles are agglutinated, i.e., mixed with the bone cement, in a smaller batch analogously to Example 1. The porosity in this batch is 20% and the compressive strength is 65 MPa.

Example 4

10 g of polymethyl methacrylate/polymethyl acrylate copolymer (52/48) are mixed intensively with 90 g of polymethyl methacrylate granules N8 (particle size≈1 mm) and 0.5 g of benzoyl peroxide in a bead mill. 50 g of this mixture are stirred with 10 ml of a mixture consisting of 60% by weight of methyl methacrylate, 20% by weight of isobornyl methacrylate and 20% by weight of decyl methacrylate (contains N,N-dimethyl-p-toluidine). A glutinous paste which can be kneaded after about 1 minute forms very rapidly. After kneading for a further minute, this material is ready for implantation. After hardening, a porous material of high compressive strength is obtained.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the preparation of porous bone replacement materials which have a partly or completely interconnecting pore system with a volume content of 5 to 60%, which comprises mixing the following components (a), (b) and (c) with one another:

(a) 0 to 48% by weight of a solid component comprising a finely divided polymer of an acrylic or methacrylic acid ester or mixture thereof,
   (b) 2 to 50% by weight of a liquid component comprising an acrylic or methacrylic acid ester monomer or mixture thereof, and
   (c) 50 to 98% by weight of coarse-particled granules of a biocompatible material having a largest particle diameter of 0.5 to 10 mm, optionally forming the mixture into a desired shape and hardening the mixture.

2. The process of claim 1, wherein the solid component (a) further comprises at least one of a polymerization catalyst, X-ray contrast medium, filler or dyestuff.

3. The process of claim 1, wherein the liquid component (b) further comprises a polymerization accelerator or stabilizer.

4. The process according to claim 1, wherein the coarse-particled granules (c) have an average particle diameter of from 1–5 mm.

5. The process of claim 1, wherein the coarse-particled granules (c) have an average particle diameter of about 3 mm.

6. The process according to claim 1, wherein the coarse-particled granules (c) have a spherical shape, approximately spherical shape or cylindrical shape.

7. The process according to claim 1, wherein the coarse-particled granules (c) are a hardened mixture of about 5 to 90% by weight of a solid component comprising a finely divided polymer of an acrylic or methacrylic acid ester or mixture thereof, and about 95 to 10% by weight of a liquid component comprising an acrylic and/or methacrylic acid ester monomer or mixture thereof.

8. The process of claim 7, wherein the solid component used to prepare the coarse-particled granules further comprises at least one of a polymerization catalyst, X-ray contrast medium filler or dye.

9. The process of claim 7, wherein the liquid component used to prepare the coarse-particled granules further comprises at least one of a polymerization accelerator or stabilizer.

10. The process according to claim 1, wherein the coarse-particled granules (c) comprise a hardened plastics material based on polyolefins, copolymers of acrylates with styrene and/or butadiene or epoxy resins.

11. The process according to claim 1, wherein the coarse-particled granules (c) are a sintered calcium phosphate ceramic.

12. The process according to claim 1, wherein the solid component (a) and/or the coarse-particled granules (c) further comprise an osteoinductive or osteoconductive filler.

13. The process according to claim 1, wherein the solid component (a) and/or the coarse-particled granules (c) further comprise a pharmaceutically active compound.

14. The process of claim 7, wherein the liquid component used to prepare the coarse-particled granules further comprises at least one of a polymerization accelerator or stabilizer.

15. The process of claim 1, wherein a solid component (a) having an average particle size of 5 to 250 µm is mixed with components (b) and (c).

* * * * *